United States Patent
Ferek-Petric

(12) 
(10) Patent No.: US 6,754,532 B1
(45) Date of Patent: Jun. 22, 2004

(54) CORONARY SINUS FLOW REGULATED PACING

(75) Inventor: Bozidar Ferek-Petric, Zagreb (HR)

(73) Assignee: Medtronic, Inc., Minneapolis, MN (US)

(*) Notice: Subject to any disclaimer, the term of this patent is extended or adjusted under 35 U.S.C. 154(b) by 0 days.

(21) Appl. No.: 09/558,867

(22) Filed: Apr. 28, 2000

(51) Int. Cl.[7] ............................................. A61N 1/36
(52) U.S. Cl. ................................ 607/17; 607/9; 607/23
(58) Field of Search ........................... 607/23, 24, 17, 607/5; 600/526

(56) References Cited

U.S. PATENT DOCUMENTS 5,213,098 A * 5/1993 Bennett et al. ............... 607/18
6,223,082 B1 * 4/2001 Bakels et al. ................ 607/17

* cited by examiner

Primary Examiner—Angela D. Sykes
Assistant Examiner—Roderick Bradford
(74) Attorney, Agent, or Firm—Girma Wolde-Michael; Paul H. McDowall

(57) ABSTRACT

An implantable system having a left ventricular pacing lead for implantation in the great cardiac vein via the coronary sinus of a patient's heart. The pacing lead includes a sensor for measuring the velocity of blood flowing through the coronary sinus. An implantable medical device (IMD) coupled to the pacing lead monitors the blood flow signal from the sensor and delivers pacing pulses to the patient's heart as a function of the blood flow signal. The IMD integrates the blood flow signal to estimate blood flow volume and adjusts a pacing parameter of the pacing pulses to maximize the blood flow. In a multi-chamber pacing system, the IMD continuously adjusts the atrial and ventricular (AV) delay in order to maximize the integral of the velocity signal received from pacing lead. In a multisite pacing system, where the IMD includes a plurality of ventricular pacing leads, the IMD adjusts the interventricular delay.

22 Claims, 9 Drawing Sheets

CORONARY SINUS FLOW REGULATED PACING

FIELD OF INVENTION

This invention relates generally to the field of implantable medical devices, and more particularly to implantable heart monitors and therapy delivery devices.

BACKGROUND

A wide variety of implantable heart monitors and therapy delivery devices have been developed including pacemakers, cardioverter/defibrillators, heart pumps, cardiomyostimulators, ischemia treatment devices, and drug delivery devices. Most of these cardiac systems include electrodes for sensing and sense amplifiers for recording and/or deriving sense event signals. Often the sense event signals are utilized to control the delivery of pacing stimuli in accordance with a predefined algorithm.

Several prior art disclosures have been made suggesting methods seeking to optimize pacing stimuli to a patient's heart including:

TABLE 1

| Country | U.S. Pat. No. | Inventor/Applicant | Issue Date |
| --- | --- | --- | --- |
| U.S.A. | 5,514,163 | Markowitz et al | 1996 |
| U.S.A. | 4,303,075 | Heilman et al | 1981 |
| U.S.A. | 5,243,976 | Ferek-Petric et al | 1993 |
| U.S.A. | 5,318,595 | Ferek-Petric et al | 1994 |

All patents listed in Table 1 above are hereby incorporated by reference herein in their respective entireties. As those of ordinary skill in the art will appreciate readily upon reading the Summary of the Invention, Detailed Description and Claims set forth below, many of the devices and methods disclosed in the patents of Table 1 may be modified advantageously by using the teachings of the present invention.

SUMMARY OF THE INVENTION

In general, the invention provides an implantable medical device system designed to optimize blood flow through the coronary artery of a patient's heart by monitoring blood exiting through the coronary sinus. The invention provides solutions to problems existing in the prior art by providing closed loop regulation of pacing stimuli in response to sensed blood velocity through the coronary sinus so as to maximize oxygen supply to the cardiac muscle.

According to one feature, an implantable medical device system includes a left ventricular pacing lead for implantation in the great cardiac vein via the coronary sinus of a patient's heart. The pacing lead includes a flow sensor for measuring the velocity of blood flowing through the coronary sinus. An implantable medical device (IMD) coupled to the pacing lead monitors a blood flow signal from the sensor and delivers pacing pulses to the patient's heart as a function of the blood flow signal. The IMD calculates the integral of the blood flow signal to estimate blood flow volume and adjusts a pacing parameter of pacing pulses delivered to the heart in order to maximize the blood flow.

The features of the invention may be incorporated in a variety of embodiments. For example, in one configuration, the IMD continuously adjusts the atrial and ventricular (AV) delay in order to maximize the integral of the velocity signal received from pacing lead. In a multisite pacing system, where the IMD includes a plurality of ventricular pacing leads for pacing the left and right ventricles, the IMD can also adjusts the interventricular delay.

Various embodiments of the invention are set forth in the accompanying drawings and the description below. Other features and advantages of the invention will become apparent from the description, the drawings, and the claims.

DETAILED DESCRIPTION

Figure 1:
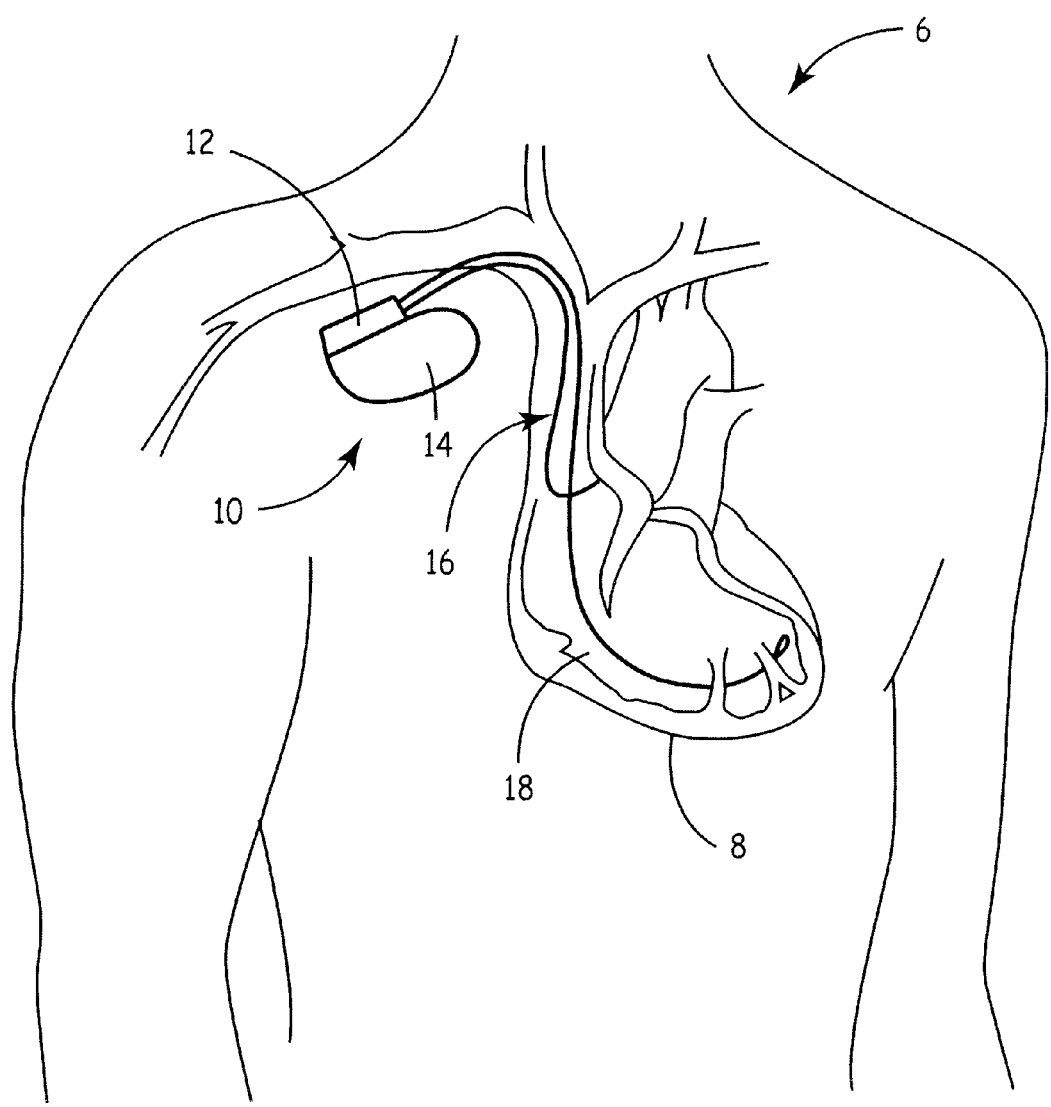
FIG. 1 illustrates an implantable medical device system in accordance with an embodiment of the invention implanted in a human body.

FIG. 1 is a simplified schematic view of one embodiment of implantable medical device ("IMD") 10 of the present invention implanted within a human body 6. IMD 10 comprises hermetically sealed enclosure 14 and connector module 12 for coupling IMD 10 to pacing and sensing leads 16 and 18 that are implanted near heart 8. Pacing and sensing leads 16 and 18 sense electrical signals attendant to the depolarization and re-polarization of the heart 8, and further provide pacing pulses for causing depolarization of cardiac tissue in the vicinity of the distal ends thereof. Leads 16 and 18 may have unipolar or bipolar electrodes disposed thereon, as is well known in the art. Examples of IMD 10 include implantable cardiac pacemakers disclosed in U.S. Pat. No. 5,158,078 to Bennett et al., U.S. Pat. No. 5,312,453 to Shelton et al. or U.S. Pat. No. 5,144,949 to Olson, all hereby incorporated by reference herein, each in its respective entirety.

Figure 2:
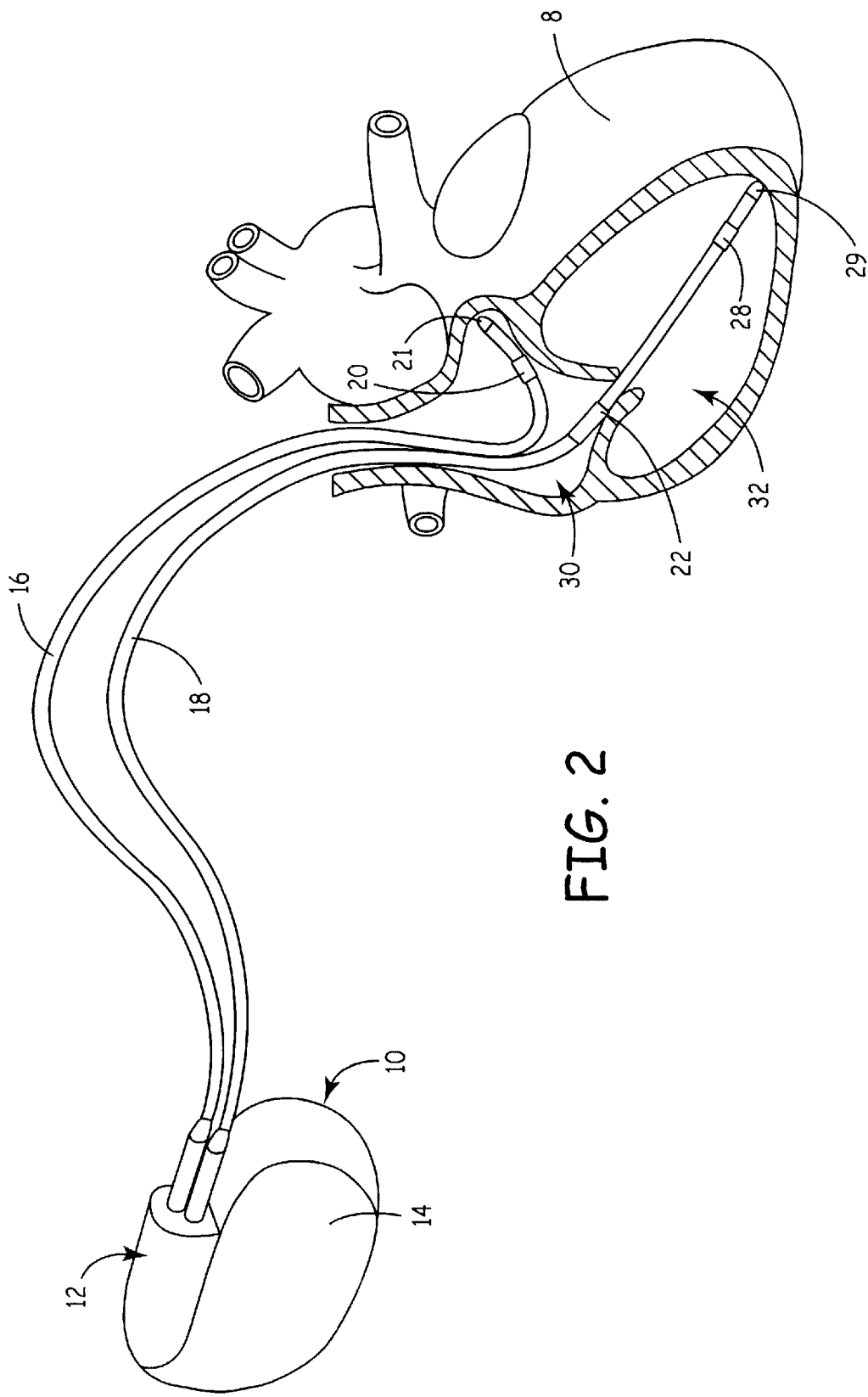
FIG. 2 illustrates one embodiment of an implantable pacemaker device system in accordance with the present invention coupled to a human heart.

FIG. 2 shows connector module 12 and hermetically sealed enclosure 14 of IMD 10 located in and near heart 8. Atrial and ventricular pacing leads 16 and 18 extend from connector module 12 to the right atrium 30 and right ventricle 32, respectively, of heart 8. Atrial electrodes 20 and 21 disposed at the distal end of atrial pacing lead 16 are located in the right atrium 30. Ventricular electrodes 28 and 29 at the distal end of ventricular pacing lead 18 are located in the right ventricle 32. Flow sensor 22 is mounted on lead 18 for measurement of the blood flow velocity within the heart.

Figure 3:
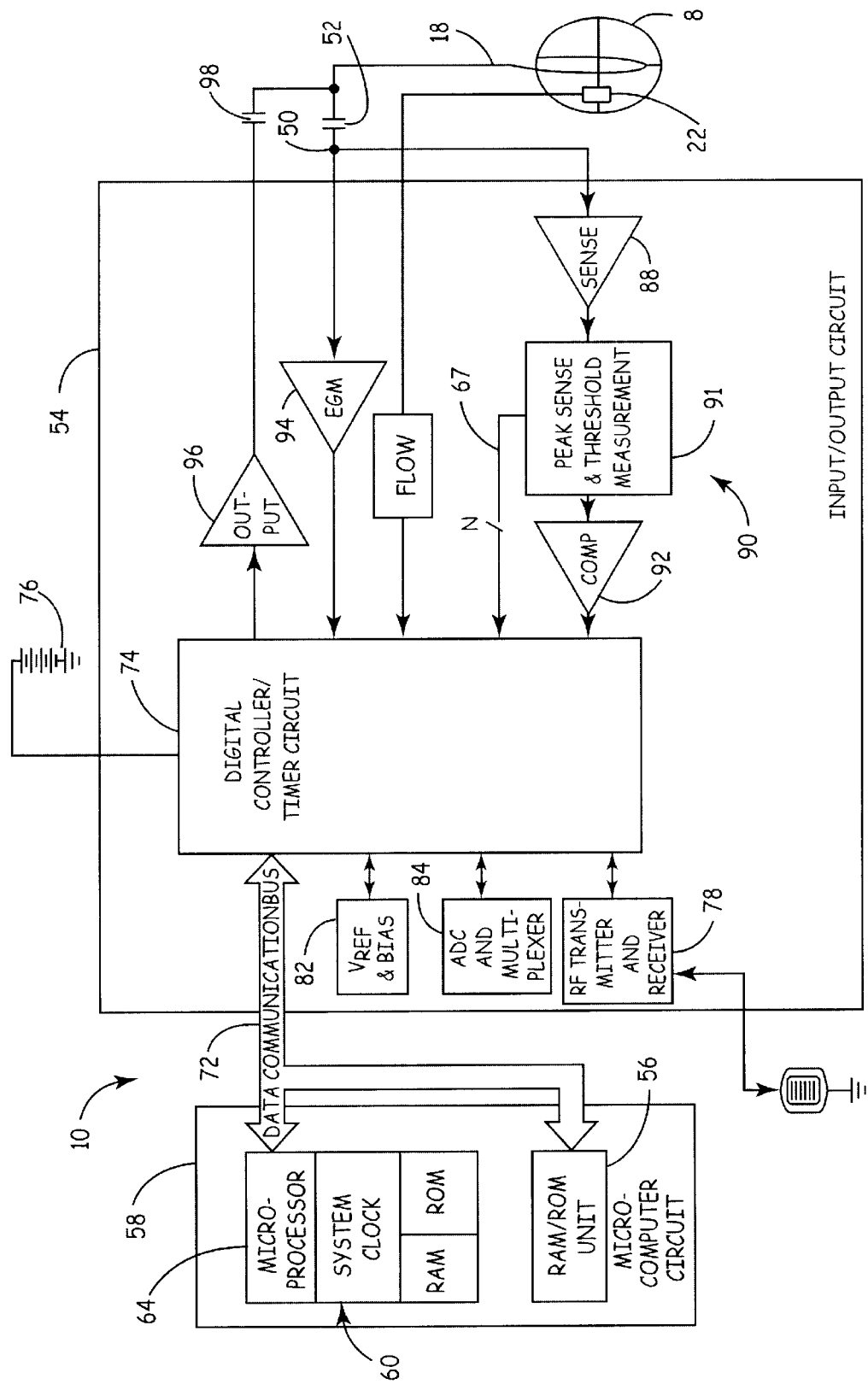
FIG. 3 is a block diagram illustrating the various components of one embodiment of an implantable pacemaker device configured to operate in accordance with the present invention.

FIG. 3 shows a block diagram illustrating the constituent components of IMD 10 in accordance with one embodiment of the present invention, where IMD 10 is pacemaker having a microprocessor-based architecture. IMD 10 is shown as including blood flow sensor 22, which is preferably electrochemical or ultrasonic Doppler mounted fixed on the lead x. Blood flow sensor 22 typically (although not necessarily) provides a flow rate signal representing the velocity of blood flowing through the heart. For the sake of convenience, IMD 10 in FIG. 3 is shown with lead 18 only connected thereto; similar circuitry and connections not explicitly shown in FIG. 3 apply to lead 16.

IMD 10 in FIG. 3 is most preferably programmable by means of an external programming unit (not shown in the figures). One such programmer is the commercially available Medtronic Model 9790 programmer, which is microprocessor-based and provides a series of encoded signals to IMD 10, typically through a programming head that transmits or telemeters radio-frequency (RF) encoded signals to IMD 10. Such a telemetry system is described in U.S. Pat. No. 5,312,453 to Wyborny et al., hereby incorporated by reference herein in its entirety. The programming methodology disclosed in Wyborny et al.'s '453 patent is identified herein for illustrative purposes only. Any of a number of suitable programming and telemetry methodologies known in the art may be employed so long as the desired information is transmitted to and from the pacemaker.

As shown in FIG. 3, lead 18 is coupled to node 50 in IMD 10 through input capacitor 52. Blood flow sensor 22 is connected to a flow signal acquisition circuit located inside hermetically sealed enclosure 14 of IMD 10. The output signal provided by flow sensor 22 is coupled to input/output circuit 54. The output signal provided by blood flow sensor 22 is coupled to input/output circuit 54. Input/output circuit 54 contains analog circuits for interfacing to heart 8, blood flow sensor 22, antenna 56 and circuits for the application of stimulating pulses to heart 8. The rate of heart 8 is controlled by software-implemented algorithms stored in microcomputer circuit 58.

Microcomputer circuit 58 preferably comprises on-board circuit 60 and off-board circuit 62. Circuit 58 may correspond to a microcomputer circuit disclosed in U.S. Pat. No. 5,312,453 to Shelton et al., hereby incorporated by reference herein in its entirety. On-board circuit 60 preferably includes microprocessor 64, system clock circuit 66 and on-board RAM 68 and ROM 70. Off-board circuit 62 preferably comprises a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components.

Electrical components shown in FIG. 3 are powered by an appropriate implantable battery power source 76 in accordance with common practice in the art. For the sake of clarity, the coupling of battery power to the various components of IMD 10 is not shown in the Figures. Antenna 56 is connected to input/output circuit 54 to permit uplink/downlink telemetry through RF transmitter and receiver telemetry unit 78. By way of example, telemetry unit 78 may correspond to that disclosed in U.S. Pat. No. 4,566,063 issued to Thompson et al., hereby incorporated by reference herein in its entirety, or to that disclosed in the above-referenced '453 patent to Wyborny et al. It is generally preferred that the particular programming and telemetry scheme selected permit the entry and storage of cardiac rate-response parameters. The specific embodiments of antenna 56, input/output circuit 54 and telemetry unit 78 presented herein are shown for illustrative purposes only, and are not intended to limit the scope of the present invention.

Continuing to refer to FIG. 3, VREF and Bias circuit 82 most preferably generates stable voltage reference and bias currents for analog circuits included in input/output circuit 54. Analog-to-digital converter (ADC) and multiplexer unit 84 digitizes analog signals and voltages to provide "real-time" telemetry intracardiac signals and battery end-of-life (EOL) replacement functions. Operating commands for controlling the timing of IMD 10 are coupled by data bus 72 to digital controller/timer circuit 74, where digital timers and counters establish an overall escape interval of the IMD 10 as well as various refractory, blanking and other timing windows for controlling the operation of peripheral components disposed within input/output circuit 54.

Digital controller/timer circuit 74 is preferably coupled to sensing circuitry 91, including sense amplifier 88, peak sense and threshold measurement unit 90 and comparator/threshold detector 92. Digital controller/timer circuit 74 is further preferably coupled to electrogram (EGM) amplifier 94 for receiving amplified and processed signals sensed by lead 18. Sense amplifier 88 amplifies sensed electrical cardiac signals and provides an amplified signal to peak sense and threshold measurement circuitry 90, which in turn provides an indication of peak sensed voltages and measured sense amplifier threshold voltages on multiple conductor signal path 67 to digital controller/timer circuit 74. An amplified sense amplifier signal is then provided to comparator/threshold detector 92. By way of example, sense amplifier 88 may correspond to that disclosed in U.S. Pat. No. 4,379,459 to Stein, hereby incorporated by reference herein in its entirety.

The electrogram signal provided by EGM amplifier 94 is employed when IMD 10 is being interrogated by an external programmer to transmit a representation of a cardiac analog electrogram. See, for example, U.S. Pat. No. 4,556,063 to Thompson et al., hereby incorporated by reference herein in its entirety. Output pulse generator 96 provides pacing stimuli to patient's heart 8 through coupling capacitor 98 in response to a pacing trigger signal provided by digital controller/timer circuit 74 each time the escape interval times out, an externally transmitted pacing command is received or in response to other stored commands as is well known in the pacing art. By way of example, output amplifier 96 may correspond generally to an output amplifier disclosed in U.S. Pat. No. 4,476,868 to Thompson, hereby incorporated by reference herein in its entirety.

The specific embodiments of input amplifier 88, output amplifier 96 and EGM amplifier 94 identified herein are presented for illustrative purposes only, and are not intended to be limiting in respect of the scope of the present invention. The specific embodiments of such circuits may not be critical to practicing some embodiments of the present invention so long as they provide means for generating a stimulating pulse and are capable of providing signals indicative of natural or stimulated contractions of heart 8.

In some preferred embodiments of the present invention, IMD 10 may operate in various non-rate-responsive modes, including, but not limited to, DDD, DDI, VVI, VOO and VVT modes. In other preferred embodiments of the present invention, IMD 10 may operate in various rate-responsive, including, but not limited to, DDDR, DDIR, VVIR, VOOR and VVTR modes. Measurement of the blood flow parameters, for example, can yield rate-responsive pacing. Some embodiments of the present invention are capable of operating in both non-rate-responsive and rate responsive modes. Moreover, in various embodiments of the present invention, IMD 10 may be programmably configured to operate so that it varies the rate at which it delivers stimulating pulses to heart 8 only in response to one or more selected sensor outputs being generated. Numerous pacemaker features and functions not explicitly mentioned herein may be incorporated into IMD 10 while remaining within the scope of the present invention.

The present invention is not limited in scope to single-sensor or dual-sensor pacemakers, and is not limited to IMD's comprising activity or pressure sensors only. Nor is the present invention limited in scope to single-chamber pacemakers,single-chamber leads for pacemakers or single-sensor or dual-sensor leads for pacemakers. Thus, various embodiments of the present invention may be practiced in conjunction with more than two leads or with multiple-chamber pacemakers, for example. At least some embodiments of the present invention may be applied equally well in the contexts of single-, dual-, triple- or quadruple-chamber pacemakers or other types of IMD's. See, for example, U.S. Pat. No. 5,800,465 to Thompson et al., hereby incorporated by reference herein in its entirety, as are all U.S. Patents referenced therein.

IMD 10 may also be a pacemaker-cardioverter-defibrillator ("PCD") corresponding to any of numerous commercially available implantable PCD's. Various embodiments of the present invention may be practiced in conjunction with PCD's such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless and U.S. Pat. No. 4,.821,723 to Baker et al., all hereby incorporated by reference herein, each in its respective entirety.

Figure 4:
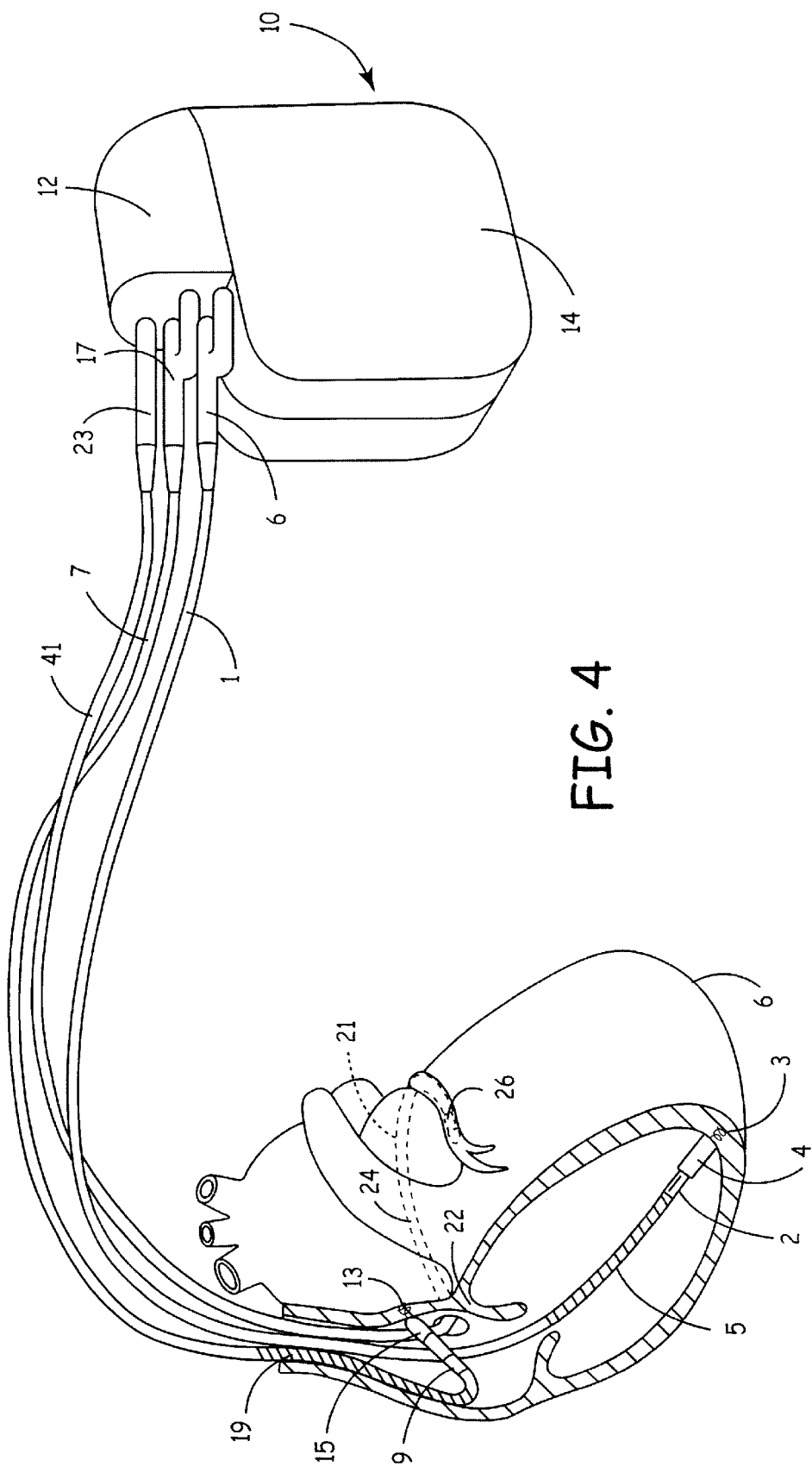
FIG. 4 illustrates one embodiment of an implantable pacemaker cardioverter defibrillator in accordance with the present invention coupled to a human heart.
Figure 5:
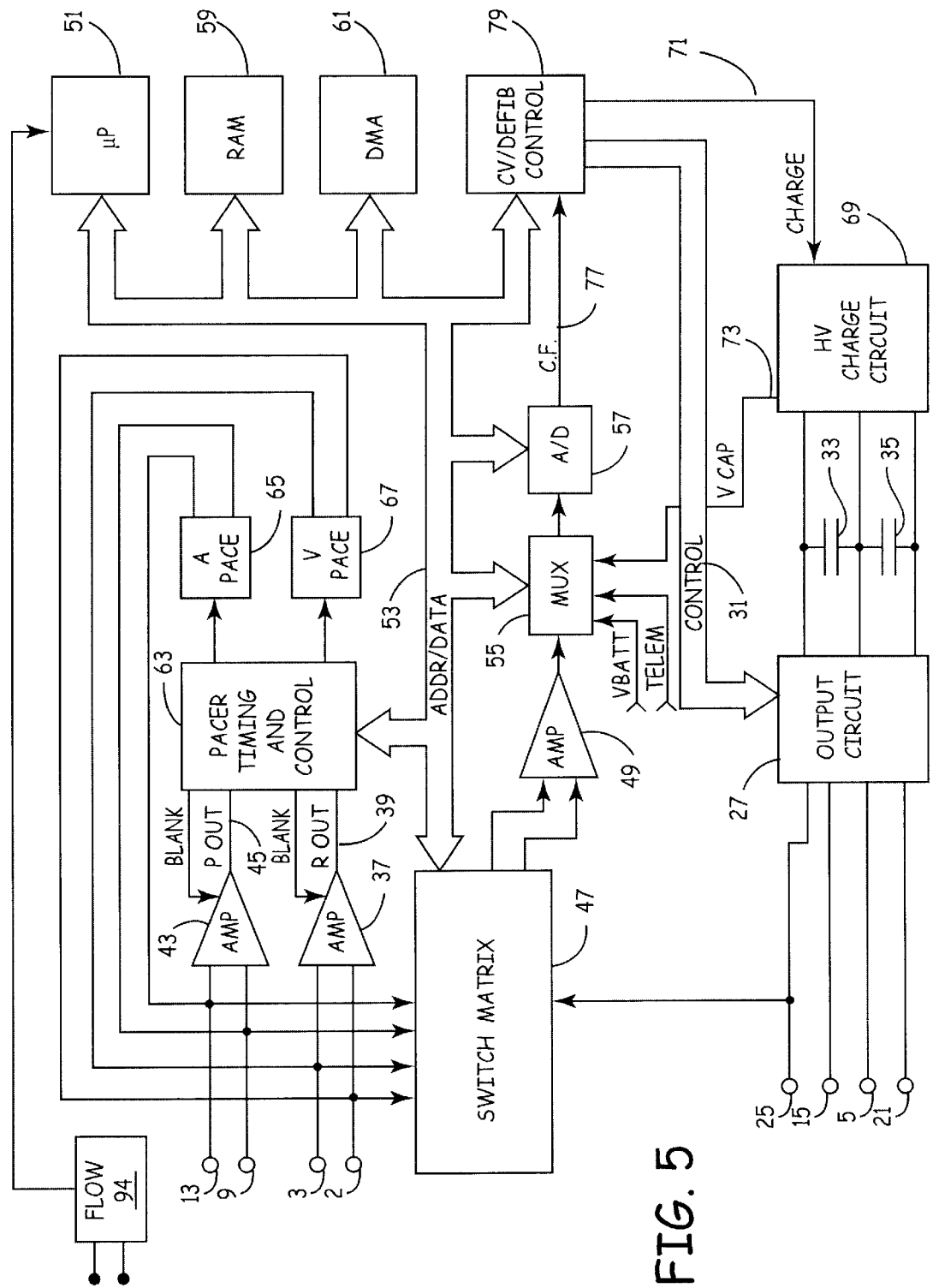
FIG. 5 is a block diagram illustrating the various components of one embodiment of an implantable pacemaker cardioverter defibrillator configured to operate in accordance with the present invention.

FIGS. 4 and 5 illustrate one embodiment in which IMD 10 is a multisite pacing system including multiple leads for providing pacing stimuli to the right atrial, the right ventricle and the surface of the left ventricle. In FIG. 4, the right ventricular lead 1 can take the form of leads disclosed in U.S. Pat. Nos. 5,099,838 and 5,314,430 to Bardy, and includes an elongated insulative lead body 1 carrying three concentric coiled conductors separated from one another by tubular insulative sheaths. Located adjacent the distal end of lead 1 are ring electrode 2, extendable helix electrode 3 mounted retractably within insulative electrode head 4 and elongated coil electrode 5. Each of the electrodes is coupled to one of the coiled conductors within lead 1. Electrodes 2 and 3 are employed for cardiac pacing and for sensing ventricular depolarizations. At the proximal end of the lead is bifurcated connector 6 which carries three electrical connectors, each coupled to one of the coiled conductors. Defibrillation electrode may be fabricated from platinum, platinum alloy or other materials known to be usable in implantable defibrillation electrodes and may be about 5 cm in length.

The right atrial lead 7 shown in FIG. 4 includes elongated insulative body carrying three concentric coiled conductors separated from one another by tubular insulative sheaths corresponding to the structure of the ventricular lead. Located adjacent the J-shaped distal end of the lead are ring electrode 9 and extendable helix electrode 13 mounted retractably within an insulative electrode head 15. Each of the electrodes is coupled to one of the coiled conductors within the lead body . Electrodes 13 and 9 are employed for atrial pacing and for sensing atrial depolarizations. Elongated coil electrode 19 is provided proximal to electrode 9 and coupled to the third conductor within the lead body.

Electrode 19 preferably is 10 cm in length or greater and is configured to extend toward the tricuspid valve. In one embodiment of the present invention, approximately 5 cm of the right atrium electrode is located in the right atrium with the remaining 5 cm located in the SVC. At the proximal end of the lead is bifurcated connector 17 carrying three electrical connectors, each coupled to one of the coiled conductors.

The left ventricular pacing lead 41 shown in FIG. 4 is located within the coronary sinus and great vein of heart 8 and, in one configuration, can provide pacing stimuli to a surface of the left ventricle of heart 8. Left ventricular pacing lead 41 is inserted such that a blood flow sensor 22 within pacing electrode 41 produces a signal representing the flow rate of blood through the coronary sinus. In one configuration, left ventricular pacing lead 41 is a bipolar lead that includes an indifferent electrode 24 and an active electrode 26 for delivering pacing pulses. In another configuration, left ventricular pacing lead 41 is a unipolar lead having a single pacing electrode at the distal end of the lead. At the proximal end of the lead is connector plug 23 carrying an electrical connector coupled to the coiled conductor.

Implantable PCD 10 is shown in FIG. 4 in combination with leads 1, 7 and 41, and lead connector assemblies 23,17 and 6 inserted into connector block 12. Optionally, insulation of the outward facing portion of housing 14 of PCD 10 may be provided using a plastic coating such as parylene or silicone rubber, as is employed in some unipolar cardiac pacemakers. The outward facing portion, however, may be left uninsulated or some other division between insulated and uninsulated portions may be employed. The uninsulated portion of housing 14 serves as a subcutaneous defibrillation electrode to defibrillate either the atria or ventricles. Lead configurations other that those shown in FIG. 4 may be practiced in conjunction with the present invention, such as those shown in U.S. Pat. No. 5,690,686 to Min et al., hereby incorporated by reference herein in its entirety.

FIG. 5 is a functional schematic diagram of one embodiment of implantable PCD 10 of the present invention. This diagram should be taken as exemplary of the type of device in which various embodiments of the present invention may be embodied, and not as limiting, as it is believed that the invention may be practiced in a wide variety of device implementations, including cardioverter and defibrillators which do not provide anti-tachycardia pacing therapies.

IMD 10 is provided with an electrode system. If the electrode configuration of FIG. 4 is employed, the correspondence to the illustrated electrodes is as follows. Electrode 25 in FIG. 5 includes the uninsulated portion of the housing of PCD 10. Electrodes 25, 15, 21 and 5 are coupled to high voltage output circuit 27, which includes high voltage switches controlled by CV/defib control logic 79 via control bus 31. Switches disposed within circuit 27 determine which electrodes are employed and which electrodes are coupled to the positive and negative terminals of the capacitor bank (which includes capacitors 33 and 35) during delivery of defibrillation pulses.

Electrodes 2 and 3 are located on or in the ventricle and are coupled to the R-wave amplifier 37, which preferably takes the form of an automatic gain controlled amplifier providing an adjustable sensing threshold as a function of the measured R-wave amplitude. A signal is generated on R-out line 39 whenever the signal sensed between electrodes 2 and 3 exceeds the present sensing threshold.

Electrodes 9 and 13 are located on or in the atrium and are coupled to the P-wave amplifier 43, which preferably also takes the form of an automatic gain controlled amplifier providing an adjustable sensing threshold as a function of the measured P-wave amplitude. A signal is generated on P-out line 45 whenever the signal sensed between electrodes 9 and 13 exceeds the present sensing threshold. The general operation of R-wave and P-wave amplifiers 37 and 43 may correspond to that disclosed in U.S. Pat. No. 5,117,824, by Keimel et al., issued Jun. 2, 1992, for "An Apparatus for Monitoring Electrical Physiologic Signals", hereby incorporated by reference herein in its entirety.

Flow acquisition circuit 94 acquires input signal from flow sensor 22, such as a ultrasonic Doppler transducer or of an electrochemical flow sensor, and provides digitized flow data to microprocessor 51 for further blood flow calculations.

Switch matrix 47 is used to select which of the available electrodes are coupled to wide band (0.5–200 Hz) amplifier 49 for use in digital signal analysis. Selection of electrodes is controlled by the microprocessor 51 via data/address bus 53, which selections may be varied as desired. Signals from the electrodes selected for coupling to bandpass amplifier 49 are provided to multiplexer 55, and thereafter converted to multi-bit digital signals by A/D converter 57, for storage in random access memory 59 under control of direct memory access circuit 61. Microprocessor 51 may employ digital signal analysis techniques to characterize the digitized signals stored in random access memory 59 to recognize and classify the patient's heart rhythm employing any of the numerous signal processing methodologies known to the art.

The remainder of the circuitry is dedicated to the provision of cardiac pacing, cardioversion and defibrillation therapies, and, for purposes of the present invention may correspond to circuitry known to those skilled in the art. The following exemplary apparatus is disclosed for accomplishing pacing, cardioversion and defibrillation functions. Pacer timing/control circuitry 63 preferably includes programmable digital counters which control the basic time intervals associated with DDD, VVI, DVI, VDD, AAI, DDI and other modes of single and dual chamber pacing well known to the art. Circuitry 63 also preferably controls escape intervals associated with anti-tachyarrhythmia pacing in both the atrium and the ventricle, employing any anti-tachyarrhythmia pacing therapies known to the art.

Intervals defined by pacing circuitry 63 include atrial and ventricular (AV) pacing escape intervals, the refractory periods during which sensed P-waves and R-waves are ineffective to restart timing of the escape intervals and the pulse widths of the pacing pulses. The durations of these intervals are determined by microprocessor 51, in response to stored data in memory 59 and are communicated to pacing circuitry 63 via address/data bus 53. As described in detail below, microprocessor 51 and pacing circuitry 63 control the pacing intervals as a function of the blood flow rate signal received from flow sensor 24 of left ventricular pacing lead 41. Pacer circuitry 63 also determines the amplitude of the cardiac pacing pulses under control of microprocessor 51.

During pacing, escape interval counters within pacer timing/control circuitry 63 are reset upon sensing of R-waves and P-waves as indicated by a signals on lines 39 and 45, and in accordance with the selected mode of pacing on time-out trigger generation of pacing pulses by pacer output circuitry 65 and 67, which are coupled to electrodes 9, 13, 2 and 3. Escape interval counters are also reset on generation of pacing pulses and thereby control the basic timing of cardiac pacing functions, including anti-tachyarrhythmia pacing. The durations of the intervals defined by escape interval timers are determined by microprocessor 51 via data/address bus 53. The value of the count present in the escape interval counters when reset by sensed R-waves and P-waves may be used to measure the durations of R-R intervals, P-P intervals, P-R intervals and R-P intervals, which measurements are stored in memory 59 and used to detect the presence of tachyarrhythmias.

As explained in detail below, IMD 10 regulates the pacing pulses delivered to heart 8 as a function of the velocity of blood flowing through the coronary sinus. For example, in dual-chamber pacing systems having an atrial pacing lead 16 and a ventricular pacing 18, as illustrated in FIGS. 2 and 3, microprocessor 64 configures pacer time/control circuitry 63 to control the AV delay. The AV delay is the length of time between the delivery of an atrial pacing pulse through lead 16 and the delivery of a ventricular output pulse through lead 18. The AV delay is typically on the order to 100 milliseconds, often ranging between 120 and 150 milliseconds, and is also known as AV interval. In multisite pacing systems, as illustrated in FIGS. 4 and 5, microprocessor 51 configures the pacer time/control circuitry 63 to control the interventricular delay. The interventricular delay is the length of time between the delivery of a pacing pulse to the right ventricle through lead 1 and the delivery of a pacing pulse to the left ventricle through left ventricular pacing lead 41.

Microprocessor 51 most preferably operates as an interrupt driven device, and is responsive to interrupts from pacer timing/control circuitry 63 corresponding to the occurrence sensed P-waves and R-waves and corresponding to the generation of cardiac pacing pulses. Those interrupts are provided via data/address bus 53. Any necessary mathematical calculations to be performed by microprocessor 51 and any updating of the values or intervals controlled by pacer timing/control circuitry 63 take place following such interrupts.

Detection of atrial or ventricular tachyarrhythmias, as employed in the present invention, may correspond to tachyarrhythmia detection algorithms known in the art. For example, the presence of an atrial or ventricular tachyarrhythmia may be confirmed by detecting a sustained series of short R-R or P-P intervals of an average rate indicative of tachyarrhythmia or an unbroken series of short R-R or P-P intervals. The suddenness of onset of the detected high rates, the stability of the high rates, and a number of other factors known in the art may also be measured at this time. Appropriate ventricular tachyarrhythmia detection methodologies measuring such factors are described in U.S. Pat. No. 4,726,380 issued to Vollmann, U.S. Pat. No. 4,880,005 issued to Pless et al. and U.S. Pat. No. 4,830,006 issued to Haluska et al., all incorporated by reference herein, each in its respective entirety. An additional set of tachycardia recognition methodologies is disclosed in the article "Onset and Stability for Ventricular Tachyarrhythmia Detection in an Implantable Pacer-Cardioverter-Defibrillator" by Olson et al., published in Computers in Cardiology, Oct. 7–10, 1986, IEEE Computer Society Press, pages 167–170, also incorporated by reference herein in its entirety. Atrial fibrillation detection methodologies are disclosed in Published PCT U.S. application Ser. No. 92/02829, Publication No. WO92/18198, by Adams et al., and in the article "Automatic Tachycardia Recognition", by Arzbaecher et al., published in PACE, May–June, 1984, pp. 541–547, both of which are incorporated by reference herein in their entireties.

In the event an atrial or ventricular tachyarrhythmia is detected and an anti-tachyarrhythmia pacing regimen is desired, appropriate timing intervals for controlling generation of anti-tachyarrhythmia pacing therapies are loaded from microprocessor 51 into the pacer timing and control circuitry 63, to control the operation of the escape interval counters therein and to define refractory periods during which detection of R-waves and P-waves is ineffective to restart the escape interval counters.

Alternatively, circuitry for controlling the timing and generation of anti-tachycardia pacing pulses as described in U.S. Pat. No. 4,577,633, issued to Berkovits et al. on Mar. 25, 1986, U.S. Pat. No. 4,880,005, issued to Pless et al. on Nov. 14, 1989, U.S. Pat. No. 4,726,380, issued to Vollmann et al. on Feb. 23, 1988 and U.S. Pat. No. 4,587,970, issued to Holley et al. on May 13, 1986, all of which are incorporated herein by reference in their entireties, may also be employed.

In the event that generation of a cardioversion or defibrillation pulse is required, microprocessor 51 may employ an escape interval counter to control timing of such cardioversion and defibrillation pulses, as well as associated refractory periods. In response to the detection of atrial or ventricular fibrillation or tachyarrhythmia requiring a cardioversion pulse, microprocessor 51 activates cardioversion/defibrillation control circuitry 79, which initiates charging of the high voltage capacitors 33 and 35 via charging circuit 69, under the control of high voltage charging control line 71. The voltage on the high voltage capacitors is monitored via VCAP line 73, which is passed through multiplexer 55 and in response to reaching a predetermined value set by microprocessor 51, results in generation of a logic signal on Cap Full (CF) line 77 to terminate charging. Thereafter, timing of the delivery of the defibrillation or cardioversion pulse is controlled by pacer timing/control circuitry 63. Following delivery of the fibrillation or tachycardia therapy microprocessor 51 returns the device to q cardiac pacing mode and awaits the next successive interrupt due to pacing or the occurrence of a sensed atrial or ventricular depolarization.

Several embodiments of appropriate systems for the delivery and synchronization of ventricular cardioversion and defibrillation pulses and for controlling the timing functions related to them are disclosed in U.S. Pat. No. 5,188,105 to Keimel, U.S. Pat. No. 5,269,298 to Adams et al. and U.S. Pat. No. 4,316,472 to Mirowski et al., hereby incorporated by reference herein, each in its respective entirety. Any known cardioversion or defibrillation pulse control circuitry is believed to be usable in conjunction with various embodiments of the present invention, however. For example, circuitry controlling the timing and generation of cardioversion and defibrillation pulses such as that disclosed in U.S. Pat. No. 4,384,585 to Zipes, U.S. Pat. No. 4,949,719 to Pless et al., or U.S. Pat. No. 4,375,817 to Engle et al., all hereby incorporated by reference herein in their entireties, may also be employed.

Delivery of cardioversion or defibrillation pulses is accomplished by output circuit 27 under the control of control circuitry 79 via control bus 31. Output circuit 27 determines whether a monophasic or biphasic pulse is delivered, the polarity of the electrodes and which electrodes are involved in delivery of the pulse. Output circuit 27 also includes high voltage switches that control whether electrodes are coupled together during delivery of the pulse. Alternatively, electrodes intended to be coupled together during the pulse may simply be permanently coupled to one another, either exterior to or interior of the device housing, and polarity may similarly be pre-set, as in current implantable defibrillators. An example of output circuitry for delivery of biphasic pulse regimens to multiple electrode systems may be found in the above cited patent issued to Mehra and in U.S. Pat. No. 4,727,877, hereby incorporated by reference herein in its entirety.

An example of circuitry which may be used to control delivery of monophasic pulses is disclosed in U.S. Pat. No. 5,163,427 to Keimel, also incorporated by reference herein in its entirety. Output control circuitry similar to that disclosed in U.S. Pat. No. 4,953,551 to Mehra et al. or U.S. Pat. No. 4,800,883 to Winstrom, both incorporated by reference herein in their entireties, may also be used in conjunction with various embodiments of the present invention to deliver biphasic pulses.

Alternatively, IMD 10 may be an implantable nerve stimulator or muscle stimulator such as that disclosed in U.S. Pat. No. 5,199,428 to Obel et al., U.S. Pat. No. 5,207,218 to Carpentier et al. or U.S. Pat. No. 5,330,507 to Schwartz, or an implantable monitoring device such as that disclosed in U.S. Pat. No. 5,331,966 issued to Bennet et al., all of which are hereby incorporated by reference herein, each in its respective entirety. The present invention is believed to find wide application to any form of implantable electrical device for use in conjunction with electrical leads.

Figure 6:
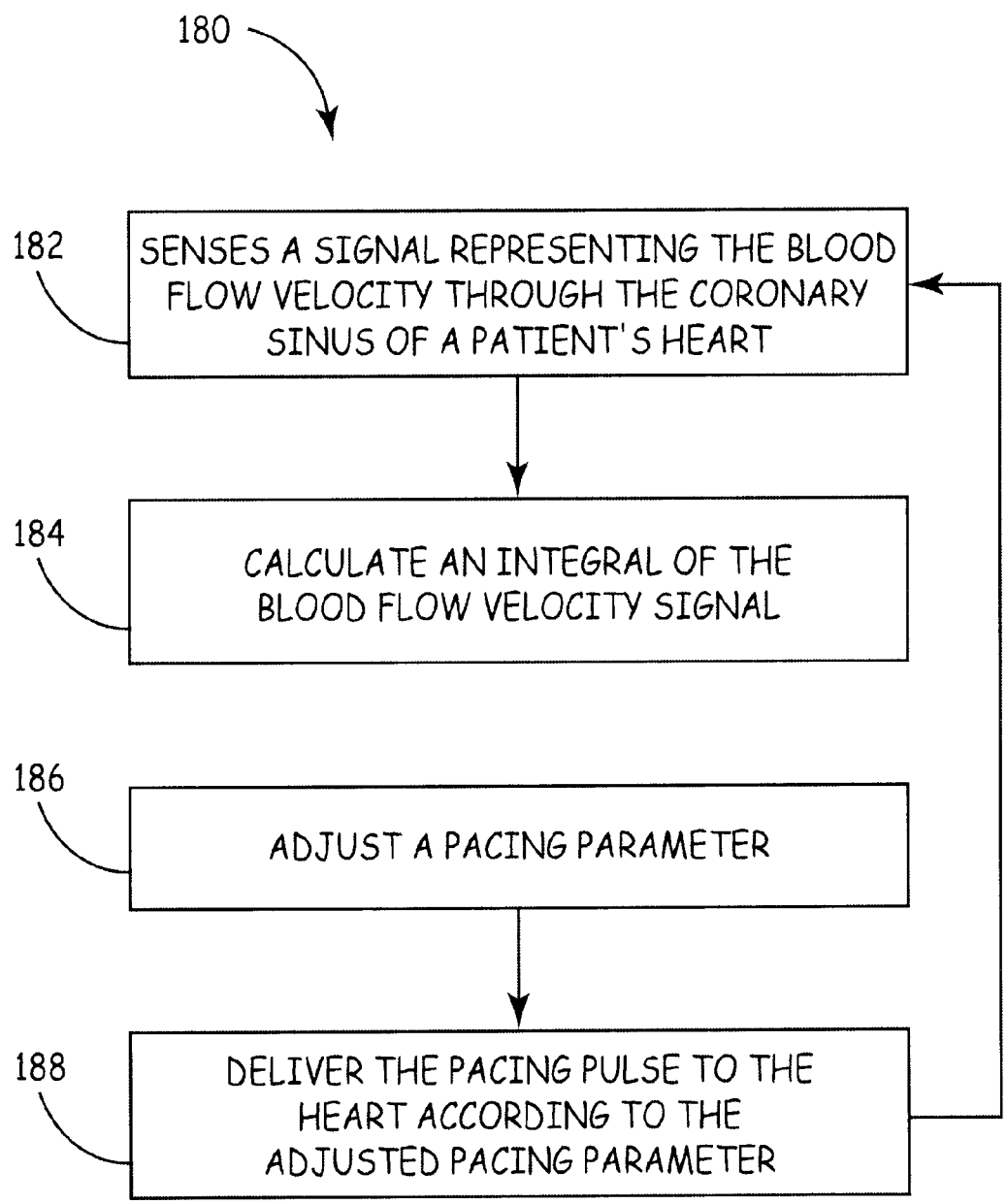
FIG. 6 is a flow chart illustrating one mode of operation of an implantable medical device operating according to the invention.

FIG. 6 is a flow chart illustrating one embodiment of a process 180 in which IMD 10 regulates the pacing pulses delivered to heart 8 as a function of the velocity of blood flowing through the coronary sinus. In general, the IMD 10 provides a closed loop regulation of the pacing pulses in order to maximize oxygen supply to the cardiac muscle of heart 8 by optimizing blood flow through the coronary artery.

Microcomputer circuit 58 senses and monitors the blood flow rate signal generated by pacing lead 41 (182). In addition, microcomputer circuit 58 continuously analyzes the flow rate signal and computes the integral of the signal (184). The resultant integral of the blood velocity can be used to estimate the volume of the blood flowing through the coronary sinus. Furthermore, because the volume of blood flowing into the arterial system must be equal to the volume flowing out of the venous system, the volume of blood through the coronary sinus can be used as an indicator of the coronary blood supply. In another embodiment, as described below, microcomputer circuit 58 calculates a duration for the blood flow through the coronary sinus.

Based on the integral of the blood flow velocity signal, IMD 10 adjusts a pacing parameter used in providing pacing stimuli to heart 8 (186). For example, in dual-chamber pacing systems, microprocessor 64 configures counters within pacer time/control circuitry 63 to adjust the AV delay. In multisite pacing systems, microprocessor 51 configures counters within pacer time/control circuitry 63 to adjust the interventricular delay.

Based on the adjusted pacing parameter, IMD 10 provides pacing stimuli such that the rate of heart 8 is paced as a function of the sensed blood flow through the coronary sinus (188). In this manner, IMD 10 provides closed-loop control of the pacing stimuli in order to optimize blood exiting through the coronary sinus, thereby maximizing blood flow through the coronary artery and ensuring maximal oxygen supply to the cardiac muscle.

Figure 7:
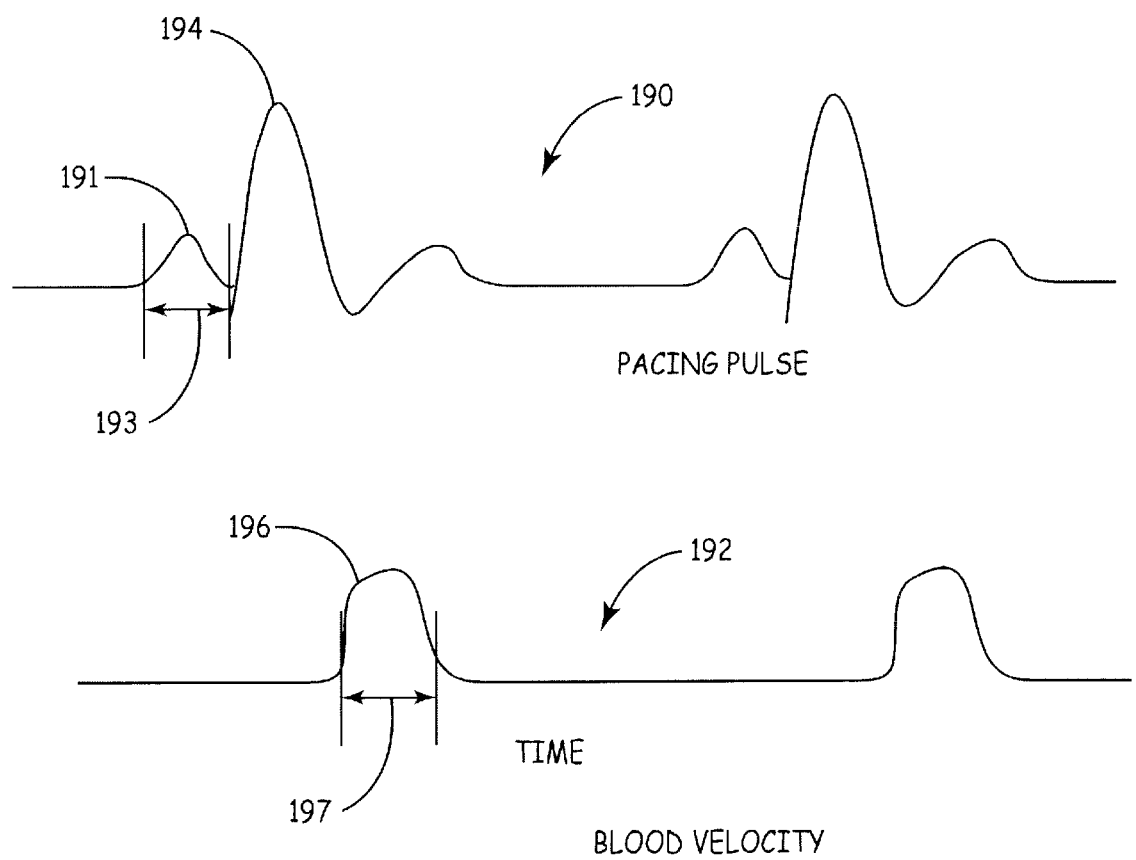
FIG. 7 illustrates a pacing pulse delivered to the right ventricle of the patient's heart in relation to the blood flow through the coronary sinus.

FIG. 7 illustrates an electrocardiogram 190 of the VDD pacing stimuli delivered to heart 8 by IMD 10 as well as a graph of the sensed signal 192 received from flow sensor 22 of left ventricular pacing lead 41 representing the velocity of blood flow through the coronary sinus of heart 8. P Wave 191 is the portion of the ECG 190 representing atrial depolarization. The AV delay 193 represents the length of time between the beginning of P wave 191 and the deliver of pacing pulse 194 to the left ventricle through pacing lead 1. Each pacing pulse 194 delivered to heart 8 results in a corresponding flow of blood through the coronary sinus, which causes a surge 196 in blood flow rate signal 192 from left ventricular pacing lead 41. For each pacing stimuli delivered to heart 8, blood flows through the coronary sinus for a duration 197.

The coronary flow is normally impeded during systole, the period during a ventricular contraction. Accordingly, duration of diastole, when the ventricle relaxes, is an important determinant of myocardial perfusion. If the diastole is prolonged, the coronary flow duration may be prolonged too. Prolongation of the diastole may be achieved by means of the AV delay shortening.

Figure 8:
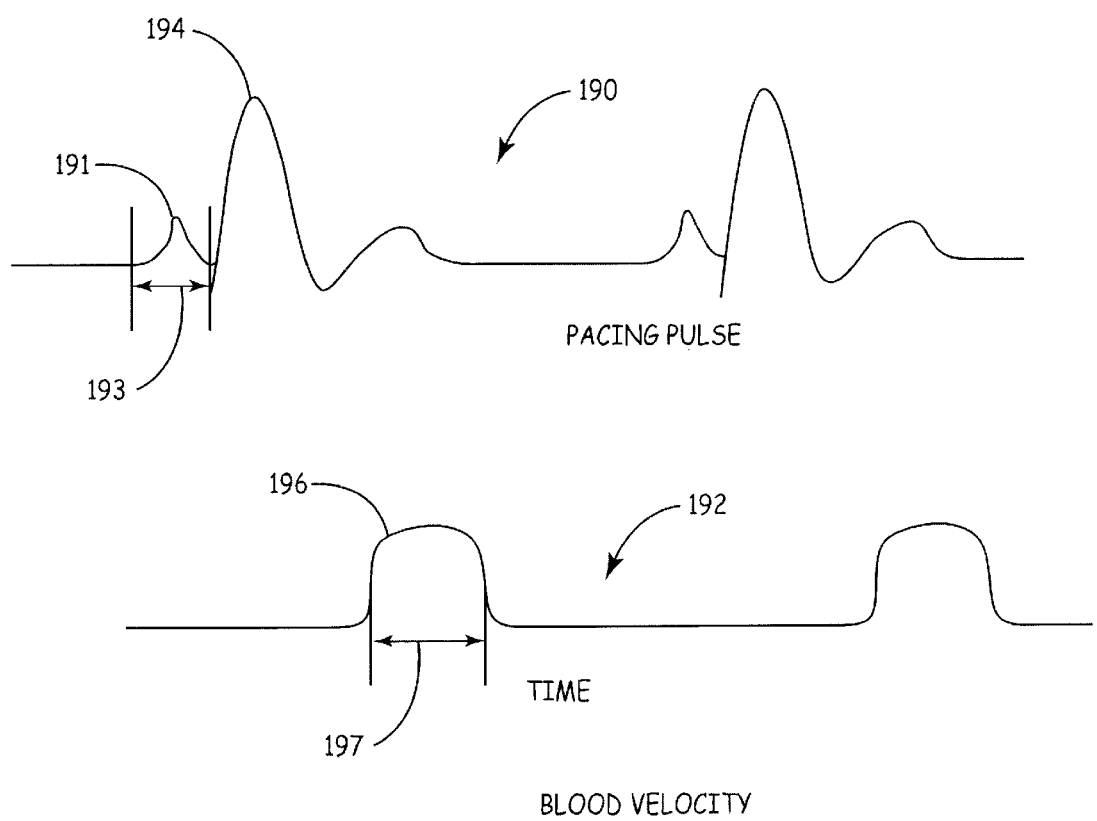
FIG. 8 illustrates how the flow of blood through the coronay sinus relates to the AV delay.

FIG. 8 illustrates electrocardiogram 190 of the VDD pacing stimuli in which the duration 197 of the flow rate signal 196 is increases due to a decrease in the AV delay 193. IMD 10 adjusts the AV delay 193 as a function of the sensed blood flood flow signal 192. In order to extend the coronary flow, IMD 10 shortens the AV delay in order to extend the diastole.

Figure 9A:
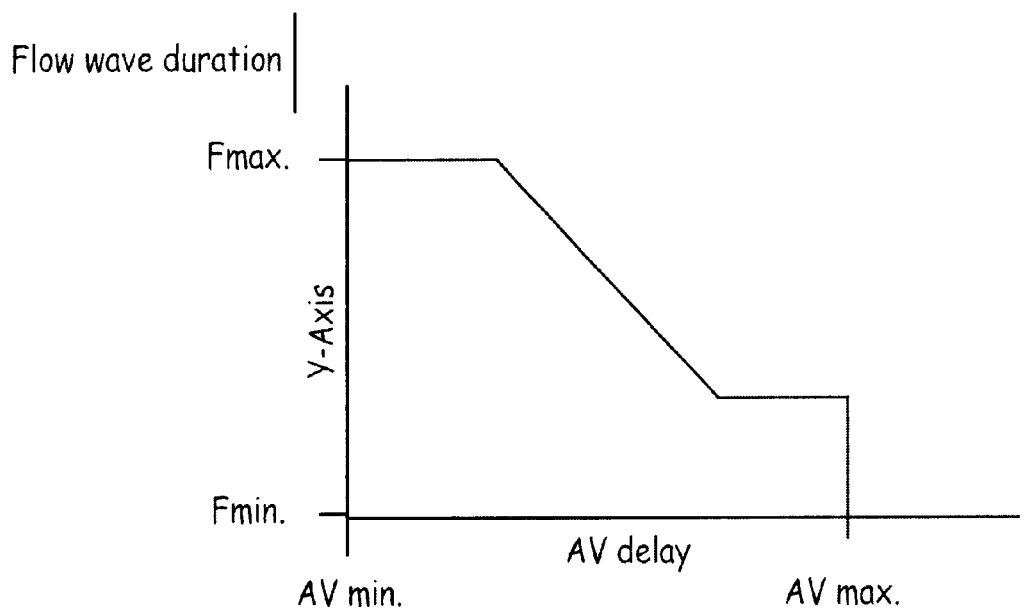
FIGS. 9A and 9B illustrate examples of AV delay regulation as a function of the coronary sinus flow.
Figure 9B:
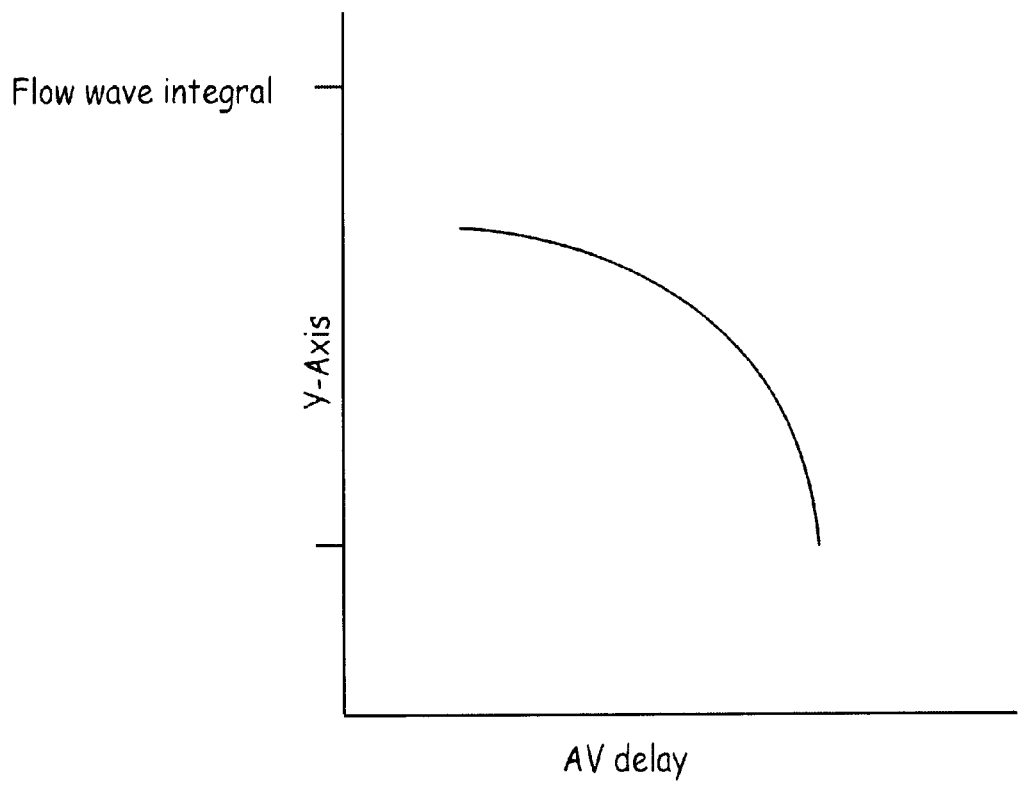

FIGS. 9A and 9B illustrates exemples of AV delay regulation as a function of the coronary sinus flow. FIG. 9A shows the duration 197 of the coronary flow wave as related to the AV delay. Changing the AV delay 193 between the minimum allowable (AV min) and maximum allowable value (AV max) causes a corresponding change in the coronary flow wave duration 197. FIG. 9B shows the flow wave integral as related to the AV delay. IMD 10 maximizes the flow integral, which is proportional to the blood volume flowing through the coronary sinus. The minimal AV delay is dependent on the rate and, therefore, pacemakers have the abilty to automatically shorten the AV interval as the pacing rate increases, referred to as rate responsive AV delay. The curve shown by FIG. 9B has a ceiling such that further shortening of the AV delay will not further increase the flow wave integral.

The preceding specific embodiments are illustrative of the practice of the invention. It is to be understood, therefore, that other expedients known to those skilled in the art or disclosed herein, may be employed without departing from the invention or scope of the appended claims. The present invention is also not limited to adjusting the escape interval per se, but may find further application for improving the delivery of pacing stimuli to a patient's heart. The present invention further includes within its scope methods of making and using the implantable medical device described above.

In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of wooden parts a nail and a screw are equivalent structures.

This application is intended to cover any adaptation or variation of the present invention. It is intended that this invention be limited only by the claims and equivalents thereof.

All printed publications, patent applications and patents referenced hereinabove are incorporated by reference herein, each in its respective entirety.

What is claimed is:

1. An implantable medical device system comprising:
   a flow sensor for measuring blood flowing through a coronary sinus of a patient's heart;
   a blood flow signal generated by the flow sensor; and
   an implantable medical device (IMD) coupled to the flow sensor, wherein the IMD is configured to output pacing pulses as a function of the blood flow signal; and
   an atrial and a ventricular pacing lead coupled to the IMD to deliver the pacing pulses to the patient's heart, wherein the IMD generates the pacing pulses as a function of the blood flow signal;
   wherein an AV delay of the pacing pulses is adjusted by the IMD as a function of the blood flow signal;
   wherein the IMD is configured to adjust the AV delay to increase a duration of blood flow through the coronary sinus.

2. An implantable medical device system comprising:
   a flow sensor for measuring blood flowing through a coronary sinus of a patient's heart;
   a blood flow signal generated by the flow sensor; and
   an implantable medical device (IMD) coupled to the flow sensor, wherein the IMD is configured to output pacing pulses as a function of the blood flow signal
   further comprising:
   a left ventricular pacing lead for implantation in the great cardiac vein via the coronary sinus of a patient's heart to deliver the pacing pulse as a function of the blood flow sensor from the IMD to a left ventricle of the patient's heart; and
   a ventricular pacing lead coupled to the IMD to deliver a ventricular pacing pulse as a function of the blood flow sensor to a right ventricle of the patient's heart.

3. An implantable medical device system comprising:
   a flow sensor for measuring blood flowing through a coronary sinus of a patient's heart;
   a blood flow signal generated by the flow sensor; and
   an implantable medical device (IMD) coupled to the flow sensor, wherein the IMD is configured to output pacing pulses as a function of the blood flow signal,
   wherein an interventricular delay interval of the pacing pulses is adjusted by the IMD as a function of the blood flow signal, and
   wherein an integral of the blood flow signal is increased by the IMD adjusting the interventricular delay interval.

4. An implantable medical device system comprising:
   a flow sensor for measuring blood flowing through a coronary sinus of a patient's heart;
   a blood flow signal generated by the flow sensor; and
   an implantable medical device (IMD) coupled to the flow sensor, wherein the IMD is configured to output pacing pulses as a function of the blood flow signal;
   wherein an interventricular delay interval of the pacing pulses is adjusted by the IMD as a function of the blood flow signal
   wherein the IMD is configured to adjust the interventricular delay interval to increase a coronary flow wave duration.

5. An implantable medical device system comprising:
   a flow sensor for measuring blood flowing through a coronary sinus of a patient's heart;
   a blood flow signal generated by the flow sensor; and an implantable medical device (IMD) coupled to the flow sensor, wherein the IMD is configured to output pacing pulses as a function of the blood flow signal, wherein the IMD is configured to calculate the integral of the blood flow signal.

6. A method for pacing a patient's heart using an implanted medical device comprising:

sensing a rate of blood flow through a coronary sinus of a patient's heart;

generating apacing Pulse as a function of the sensed rate;

adjusting a pacing parameter of the pacing pulse as a function of a blood flow signal; and adjusting the pacing parameter to increase a coronary flow wave duration.

7. A method for pacing a patient's heart using an implanted medical device comprising:

sensing a rate of blood flow through a coronary sinus of a patient's heart; and generating a pacing pulse as a function of the sensed rate, wherein generating a pacing pulse includes generating atrial and ventricular (AV) pacing pulses, the method further comprising adjusting an AV delay of the pacing pulse as a function of a blood flow signal.

8. The method of claim 7 further comprising integrating the blood flow signal, wherein adjusting the AV delay includes adjusting the AV delay to increase the integral of the blood flow signal.

9. The method of claim 8 further comprising integrating the blood flow signal, wherein adjusting the interventricular delay interval includes adjusting the interventricular delay interval to drive the integral of the blood flow signal toward a target.

10. A method for pacing a patient's heart using an implanted medical devices comprising:

sensing a rate of blood flow through a coronary sinus of a patient's heart; and generating a pacing pulse as a function of the sense rate wherein generating a pacing pulse includes generating a plurality of ventricular pacing pulses, the method further comprising adjusting an interventricular delay interval of the ventricular pacing pulses as a function of the blood flow signal.

11. A method for pacing a patient's heart using an implanted medical device comprising:

sensing a rate of blood flow through a coronary sinus of a patient's heart;

generating a pacing pulse as a function of the sensed rate; and further including implanting a left ventricular pacing lead within the coronary sinus of a patient's heart to deliver the pacing pulse as a function of a sensed rate determined by sensing the rate of blood flow through the coronary sinus of the patient's heart.

12. An implantable multi-chamber pacing system comprising:

atrial sense means for sensing signals from an atrium of a patient's heart;

ventricular sense means for sensing ventricular signals from a patient's right ventricle;

coronary sense means for sensing ventricular signals from the patent's left ventricle and for sensing a signal representing a blood flow rate through the patient's coronary sinus;

pace control means for generating and delivering pacing pulses to a plurality of chambers within the patient's heart; and means for setting and timing out an AV delay as a function of the sensed blood flow rate signal and further including analyzing means for integrating the blood flow rate signal from the coronary sense means to determine a value of the AV delay.

13. The pacemaker system of claim 12 and further including adjust means for adjusting the AV delay valve to increase the integral of the blood flow rate signal.

14. An implantable medical device system comprising:

a flow sensor for measuring blood flowing through a coronary sinus of a patient's heart;

a blood flow signal generated by the flow sensor;

an implantable medical device (IMD) coupled to the flow sensor, wherein the IMD is configured to output pacing pulses and a function of the blood flow signal; and, an interventricular delay interval of the pacing pulses is adjusted by the IMD as a function of the blood flow signal and an integral of the blood flow signal is increased by the IMD adjusting the interventricular delay interval.

15. A method for pacing a patients' heart using an implanted medical device comprising:

sensing a rate of blood flow through a coronary sinus of a patient's heart;

generating a pacing pulse as a function of the sensed rate;

adjusting a pacing parameter of the pacing pulse as a function of the blood flow signal:

calculating an integral of the blood flow signal; and adjusting the pacing parameter of the pacing pulse to drive the integral of a blood flow signal toward a target.

16. A method for pacing a patients' heart using an implanted medical device comprising:

sensing a rate of blood flow through a coronary sinus of a patient's heart;

generating a pacing pulse as a function of the sensed rate;

adjusting a pacing parameter of the pacing pulse as a function of the blood flow signal; and adjusting the pacing parameter to increase a coronary flow wave duration.

17. A method for pacing a patient's heart using an implanted medical device comprising:

sensing a rate of blood flow through a coronary sinus of a patient's heart;

generating a pacing pulse as a function of the sensed rate that includes generating atrial and ventricular (AV) pacing pulses;

adjusting an AV delay of the pacing pulse as a function of a blood flow signal; and integrating the blood flow signal, wherein adjusting the AVE delay includes adjusting the AV to increase the integral of the blood flow signal.

18. The method of claim 17 further comprising integrating the blood flow signal, wherein adjusting the interventricular delay interval includes adjusting the interventricular delay interval to drive the integral of the blood flow signal toward a target.

19. A method for pacing a patient's heart using an implanted medical device comprising:

sensing a rate of blood flow through a coronary sinus of a patient's heart; and generating a pacing pulse as a function of the sensed rate, wherein generating a pacing pulse includes generating a plurality of ventricular pacing pulses, the method further comprising adjusting an interventricular delay interval of the ventricular pacing pulses as a function of the blood flow signal.

20. A method for pacing a patient's heart using an implanted medical device comprising;

sensing a rate of blood flow through a coronary sinus of a patients heart;

generating a pacing pulse as a function of the senses rate; and, implanting a left ventricular pacing lead within the coronary sinus of a patient's heart to deliver the paving pulse as a function of the sense rate determined by sensing the rate of blood flow through the coronary sinus of the patient's heart.

21. An implantable multi-chamber pacing system comprising:

atrial sense means for sensing signals from an atrium of a patient's heart; ventricular sense means for sending ventricular signals from a patient's right ventricle;

coronary sense means for sensing ventricular signals from the patient's left ventricle and for sensing a signal representing a blood flow rate through the patient's coronary sinus;

pace control means for generating and delivering pacing pulses to a plurality of chambers within the patient's heart, wherein the pace control means includes means for setting and timing out an AV delay as a function of the sensed blood flow rate signal; and, analyzing means for integrating the blood flow signal from the coronary sense means to determine a value of the AV delay.

22. The pacemaker system of claim 21 and further including adjust means for adjusting the AV delay valve to increase the integral of the blood flow rate signal.

* * * * *

UNITED STATES PATENT AND TRADEMARK OFFICE
CERTIFICATE OF CORRECTION

PATENT NO. : 6,754,532 B1
DATED : June 22, 2004
INVENTOR(S) : Bozidar Ferek-Petric It is certified that error appears in the above-identified patent and that said Letters Patent is hereby corrected as shown below:

Column 13,
Line 11, delete "apacing Pulse" and insert -- a pacing pulse --.

Signed and Sealed this

Fifteenth Day of February, 2005

JON W. DUDAS
*Director of the United States Patent and Trademark Office*